(12) United States Patent
Mazur

(10) Patent No.: US 8,226,591 B2
(45) Date of Patent: Jul. 24, 2012

(54) APPARATUS AND METHOD FOR MONITORING AND CONTROLLING EXTRACORPOREAL BLOOD FLOW RELATIVE TO PATIENT FLUID STATUS

(75) Inventor: Daniel E. Mazur, Ann Arbor, MI (US)

(73) Assignee: Michigan Critical Care Consultants, Inc., Ann Arbor, MI (US)

( * ) Notice: Subject to any disclaimer, the term of this patent is extended or adjusted under 35 U.S.C. 154(b) by 469 days.

(21) Appl. No.: 12/536,349

(22) Filed: Aug. 5, 2009

(65) Prior Publication Data
US 2010/0036486 A1 Feb. 11, 2010

Related U.S. Application Data

(60) Provisional application No. 61/086,467, filed on Aug. 5, 2008.

(51) Int. Cl.
*A61M 1/00* (2006.01)
(52) U.S. Cl. ...................... 604/4.01; 623/3.28
(58) Field of Classification Search ............. 600/16, 600/17; 604/4.01; 623/3.28
See application file for complete search history.

(56) References Cited

U.S. PATENT DOCUMENTS

| 3,756,752 A | 9/1973 | Stenner |
| 4,515,535 A | 5/1985 | D'Silva |
| 5,281,112 A | 1/1994 | Montoya et al. |
| 5,512,042 A | 4/1996 | Montoya et al. |
| 5,658,136 A | 8/1997 | Mendler |
| 2005/0095171 A1* | 5/2005 | Fressinet et al. ............ 422/44 |
| 2006/0233648 A1 | 10/2006 | Liu et al. |
| 2008/0183287 A1* | 7/2008 | Ayre ........................ 623/3.28 |
| 2008/0319544 A1* | 12/2008 | Yaegashi .................. 623/3.28 |

FOREIGN PATENT DOCUMENTS

| EP | 0087682 | 9/1983 |
| EP | 0089122 | 9/1983 |
| EP | 0376298 | 7/1990 |
| JP | 07-506882 A | 7/1995 |
| JP | 10-511161 A | 10/1998 |
| WO | 94/03216 | 2/1994 |
| WO | 2005/042066 | 5/2005 |
| WO | 2007/064927 | 6/2007 |

* cited by examiner

*Primary Examiner* — Carl H Layno
*Assistant Examiner* — Yun Haeng H Lee
(74) *Attorney, Agent, or Firm* — Jeffrey Schox

(57) ABSTRACT

A system and method for controlling extracorporeal blood flow in a patient. The system includes a blood pump having a rotor, a plurality of rollers carried by the rotor and a pump chamber extended in tension about the rollers. A sensor measures an operating parameter of the blood pump and a controller, coupled to the sensor, calculates the flow efficiency of the blood pump based on the measured operating parameter. The controller is further configured to display the flow efficiency on the display device, and the operation of the blood pump is adjusted based on the flow efficiency when necessary.

10 Claims, 6 Drawing Sheets

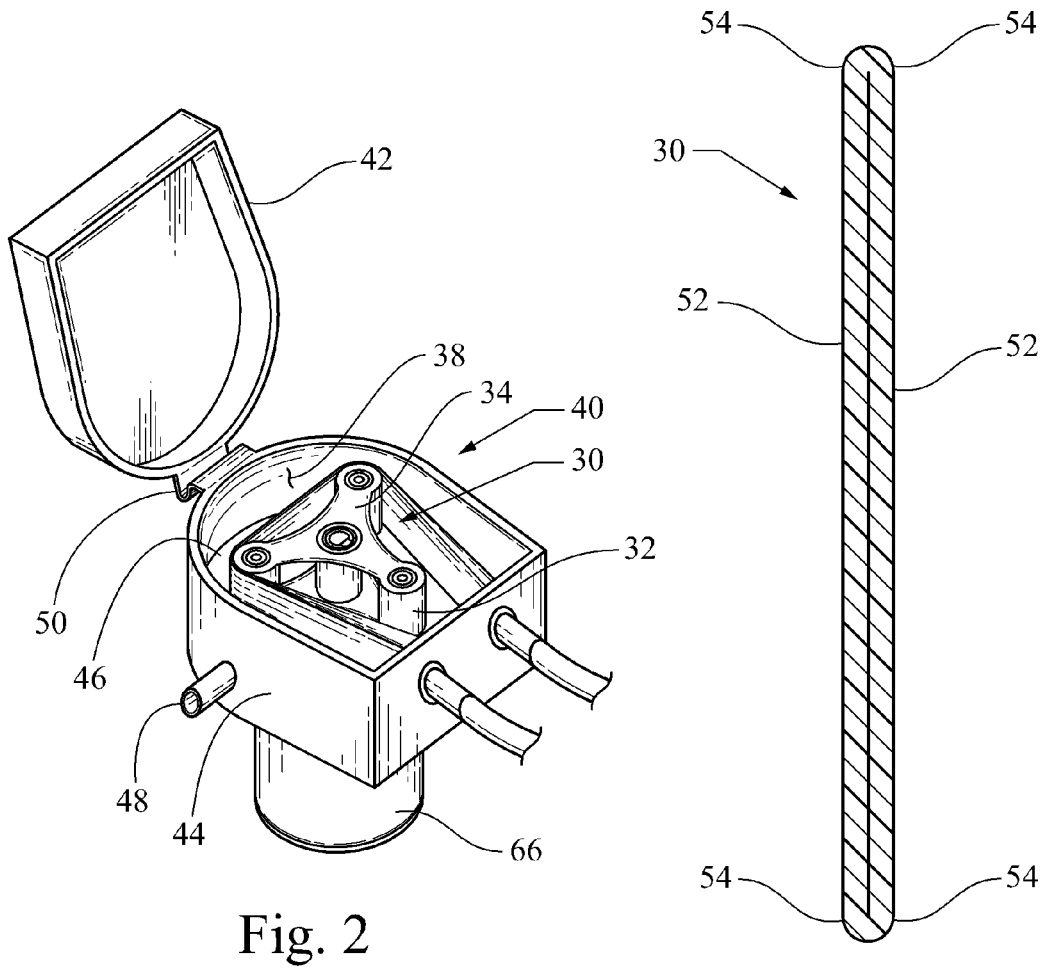
Fig. 2
Fig. 3
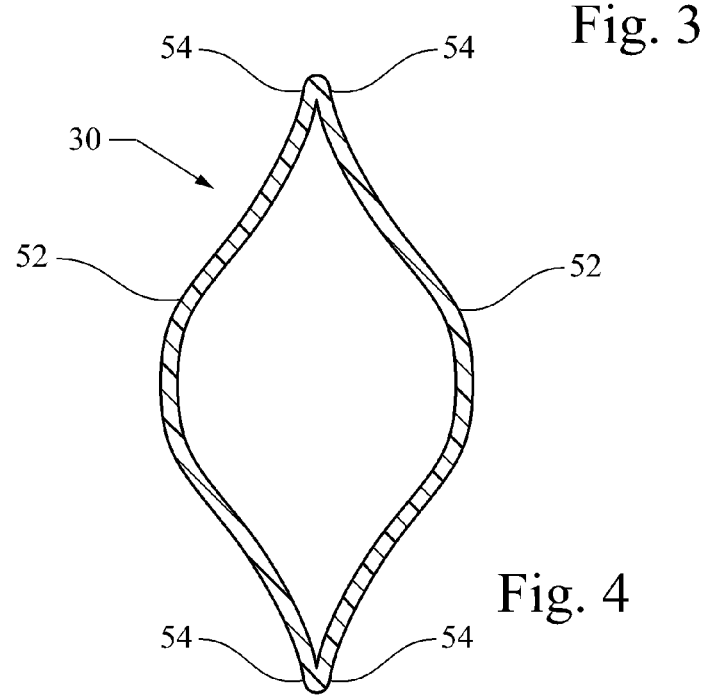
Fig. 4

| COMPONENT | MANUFACTURER | SPEC# |
|---|---|---|
| MOTOR CONTROLLER | MICROCHIP | PIC18FXX31 |
| LCD DISPLAY CONTROLLER | MICROCHIP | PIC24FXX FAMILY |
| GRAPHICS CONTROLLER | SOLOMON | SSD1905 |
| TFT DISPLAY MODULE | SOLOMON | SSD2116 |
| TFT PANEL | 320RGB X 240 | TBD |
| FLOW | EM TECH | EM "DIGIFLOW" |
| PRESSURE | UTAH MEDICAL | TBD |
| VACUUM PUMP | SCHWARZER | SP270EC |
| VACUUM CONTROLLER | MC3 | CUSTOM |
| VACUUM SENSOR | KELLER DRUCK | SERIES 2 PR |
| MOTOR | MOOG GROUP | DB SERIES TORQUER |
| POWER SUPPLY | ASTRODYNE | SWITCHING SUPPLY |
| POWER ENTRY MODULE | INTERPOWER | 83545020 |

Fig. 6

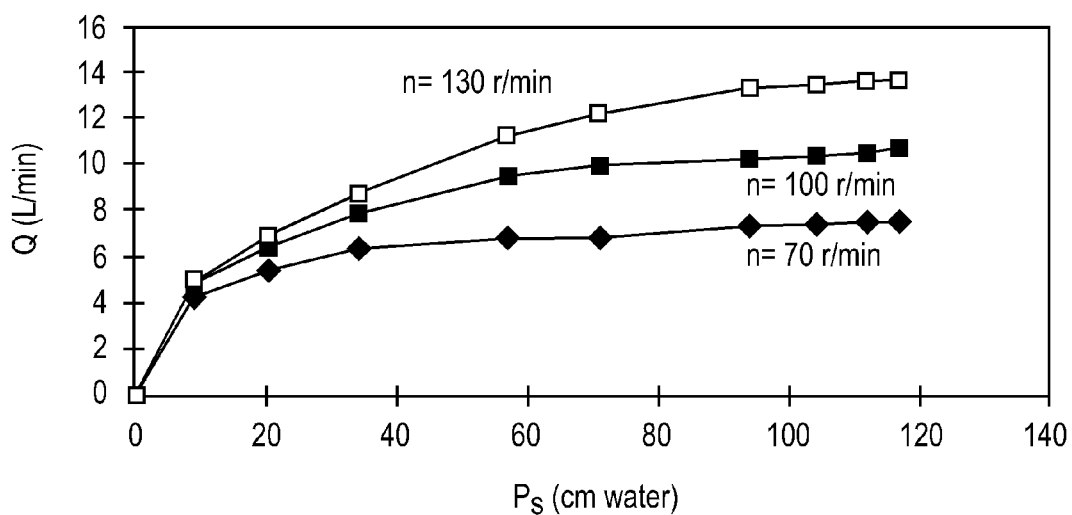

Fig. 7

APPARATUS AND METHOD FOR MONITORING AND CONTROLLING EXTRACORPOREAL BLOOD FLOW RELATIVE TO PATIENT FLUID STATUS

CROSS REFERENCE TO RELATED APPLICATIONS

The present application claims priority to U.S. provisional application entitled "Apparatus and Method for Monitoring and Achieving Optimal Extracorporeal Blood Flow Relative to Patient Fluid Status" having Application No. 61/086,467 and filed on Aug. 5, 2008.

BACKGROUND

1. Field of the Invention

The present invention generally relates to mechanical blood pumps. More specifically, the invention relates to biocompatible mechanical blood pumps for circulatory support of patients, particularly those in refractory cardiogenic shock.

2. Description of Related Technology

Cardiogenic shock occurs in a variety of clinical scenarios, including, but not limited to, acute myocardial infarction, viral myocarditis, massive pulmonary embolus, decompensated cardiomyopathy, and post cardiotomy failure. Without mechanical support, mortality is extremely high and has been reported to be from 40-80 percent. Although many patients die from multisystem organ failure, low cardiac output is likely the inciting event. The institution of circulatory support and restoration of end organ blood flow could potentially attenuate organ injury and reduce mortality.

A variety of ventricular assist devices (VADs), including blood pumps, are currently available or in clinical trials. Many of these devices are designed for intermediate or long term support, either as a bridge to heart transplantation or as destination therapy. Since these devices are implanted, they require extensive surgical procedures and are very expensive. Because of the expense and complexity of implantation, universal application of these devices to the majority of patients with cardiogenic shock is impractical.

One type of VAD, a roller pump, is frequently used in cardiopulmonary bypass and is always used in association with a venous reservoir, which ensures adequate filling of the pump. In the absence of a venous reservoir, as would be required for prolonged support, significant negative pressure (with catastrophic cavitation) can result during inadequate venous drainage. In addition, a sudden occlusion of the outflow limb of the pump will generate exceedingly high circuit pressures, risking tubing rupture. These features make roller pumps impractical for use as VADs, but they are often employed in extracorporeal membrane oxygenation (ECMO) systems, where trained perfusionists or other personnel typically oversee and operate the pump continuously. Although the disposable costs are low, labor costs for monitoring can make this type of support less cost effective.

As seen from the above, there is a need for a biocompatible, mechanical blood pump that can be used as a VAD to restore circulation in cardiogenic shock, and which is inherently safe, self regulating, nonthrombogenic, simple, durable for weeks, applicable for left, right, or bi-ventricular support, or ECMO, and for patients of any age or size. In addition, the device should be inexpensive and provide for monitoring and achieving optimal extracorporeal blood flow relative to patient fluid status.

SUMMARY OF THE INVENTION

In satisfying the above need, as well as overcoming the enumerated drawbacks and other limitations of the related art, the present invention provides a system for controlling extracorporeal blood flow in a patient. The system comprising: a blood pump including a rotor, a plurality of rollers carried by the rotor and a pump chamber extended in tension about the rollers; a sensor configured to measure an operating parameter of the blood pump; a controller coupled to the sensor, the controller calculating flow efficiency of the blood pump based on the operating parameter measured by the sensor; and a display device coupled to the controller, the controller being configured to display on the display device the flow efficiency as determined by the controller.

According to one aspect of the invention, the flow efficiency is calculated according to the equation FLOW EFFICIENCY=$(((Q \div RPM) \times (1 \div ROLLERS)) \div SV_{max}) \times 100$, wherein $SV_{max}$=the maximum stroke volume under maximum filling pressure; Q=output flow rate in liters per minute; RPM=the rotor speed in revolutions per minute; and ROLLERS=the number of rollers on the rotor.

According to another aspect of the invention, the controller is configured to graphically display the flow efficiency on the display device.

According to a further aspect of the invention, the operating parameter is output flow rate of the blood pump.

According to yet another aspect of the invention, the system includes a user input coupled to the controller and configured to adjust at least one additional operating parameter of the blood pump, including without limitation RPM of the rotor, vacuum pressure, and pump chamber tension.

According to still another aspect of the invention, the blood pump includes three rollers.

According to another aspect of the invention, the pump chamber is occluded in a free condition where the pressure acting on the interior of the pump chamber is equal to or less than the pressure acting on the exterior of the pump chamber.

According to a further aspect of the invention, the pump chamber is defined by a pair of flexible side walls joined at lateral edges thereof and defining a passageway therebetween from a pump inlet to a pump outlet.

According to yet another aspect of the invention, the system further comprising a pump enclosure defining an interior compartment, the interior compartment housing the rotor, rollers and pump chamber therein.

According to still another aspect of the invention, the pump enclosure is airtight and the interior compartment is coupled to a vacuum source.

According to a further aspect of the invention, a motor is coupled to the rotor for rotation thereof, the controller being configured to control rotation of the rotor via the motor, the motor being a DC brushless motor.

According to still another aspect of the invention, the controller is configured to display the rotational speed of the rotor on the display device.

According to another aspect of the invention, a method is provided for controlling an extracorporeal blood flow system, the method comprising: providing a extracorporeal blood flow system including a blood pump having a rotor, a plurality of rollers carried by the rotor and a pump chamber extended in tension about the rollers, a sensor configured to measure an operating parameter of the blood pump, a display device, a user interface, and a controller coupled to the sensor, the blood pump, the user interface and the display device; measuring an operating parameter of the blood pump; calculating flow efficiency of the blood pump based on the measured operating parameter; displaying flow efficiency on the display device as determined by the controller; and varying the rotational speed of blood pump based on the flow efficiency.

According to yet a further aspect of the invention, the flow efficiency is calculated according to the equation FLOW EFFICIENCY=$(((Q \div RPM) \times (1 \div ROLLERS)) \div SV_{max}) \times 100$, wherein $SV_{max}$=the maximum stroke volume under maximum filling pressure; Q=output flow rate in liters per minute; RPM=the rotor speed in revolutions per minute; and ROLLERS=the number of rollers on the rotor.

According to another aspect of the invention, the displaying of the flow efficiency on the display device is done in graphical form.

According to yet another aspect of the invention, the measured operating parameter is output flow rate of the blood pump.

According to still another aspect of the invention, the method further comprising the step of applying a vacuum to the exterior of the pump chamber.

According to a further aspect of the invention, a method of treating a patient using an extracorporeal blood flow system is provided. The method comprising: providing a extracorporeal blood flow system including a blood pump having a rotor, a plurality of rollers carried by the rotor and a pump chamber extended in tension about the rollers, a sensor configured to measure an operating parameter of the blood pump, a display device, a user interface, and a controller coupled to the sensor, the blood pump, the user interface and the display device; connecting the blood pump of the extracorporeal blood flow system to the vascular system of the patient; measuring an operating parameter of the blood pump; calculating flow efficiency of the blood pump based on the measured operating parameter; displaying the flow efficiency on the display device as determined by the controller; and varying the rotational speed of blood pump based on the flow efficiency.

According to another aspect of the invention, the treating method determines the flow efficiency according to the equation FLOW EFFICIENCY=$(((Q \div RPM) \times (1 \div ROLLERS)) \div SV_{max}) \times 100$, wherein $SV_{max}$=the maximum stroke volume under maximum filling pressure; Q=output flow rate in liters per minute; RPM=the rotor speed in revolutions per minute; and ROLLERS=the number of rollers on the rotor.

According to still another aspect of the invention, the treating method displays the flow efficiency on the display device is in graphical form.

According to yet another aspect of the invention, in the treating method the measured operating parameter is output flow rate of the blood pump.

According to a further aspect of the invention, the treating method further comprises the step of applying a vacuum to the exterior of the pump chamber.

Further objects, features and advantages of this invention will become readily apparent to persons skilled in the art after a review of the following description, with reference to the drawings and claims, which are appended to and form a part of this specification.

BRIEF DESCRIPTION OF THE DRAWINGS

FIG. 2 is perspective view of ventricular assist device, according to the principles of the present invention, with its enclosure opened to show the interior compartment and components located therein;

FIG. 3 is a cross sectional view of the pump chamber in its occluded and free condition, where the pressure inside the pump chamber is equal to or less than the pressure on the exterior of the pump chamber;

FIG. 4 is a cross sectional view of the pump chamber in its pressurized condition, where the pressure inside the pump chamber is greater than the pressure on the exterior of the pump chamber;

FIG. 6 is a table listing various components as may be included in the control unit of an embodiment of the present invention;

FIG. 7 is a graph of the relationship between inlet pressure and flow rate at various rotor speeds;

DETAILED DESCRIPTION

Figure 1:
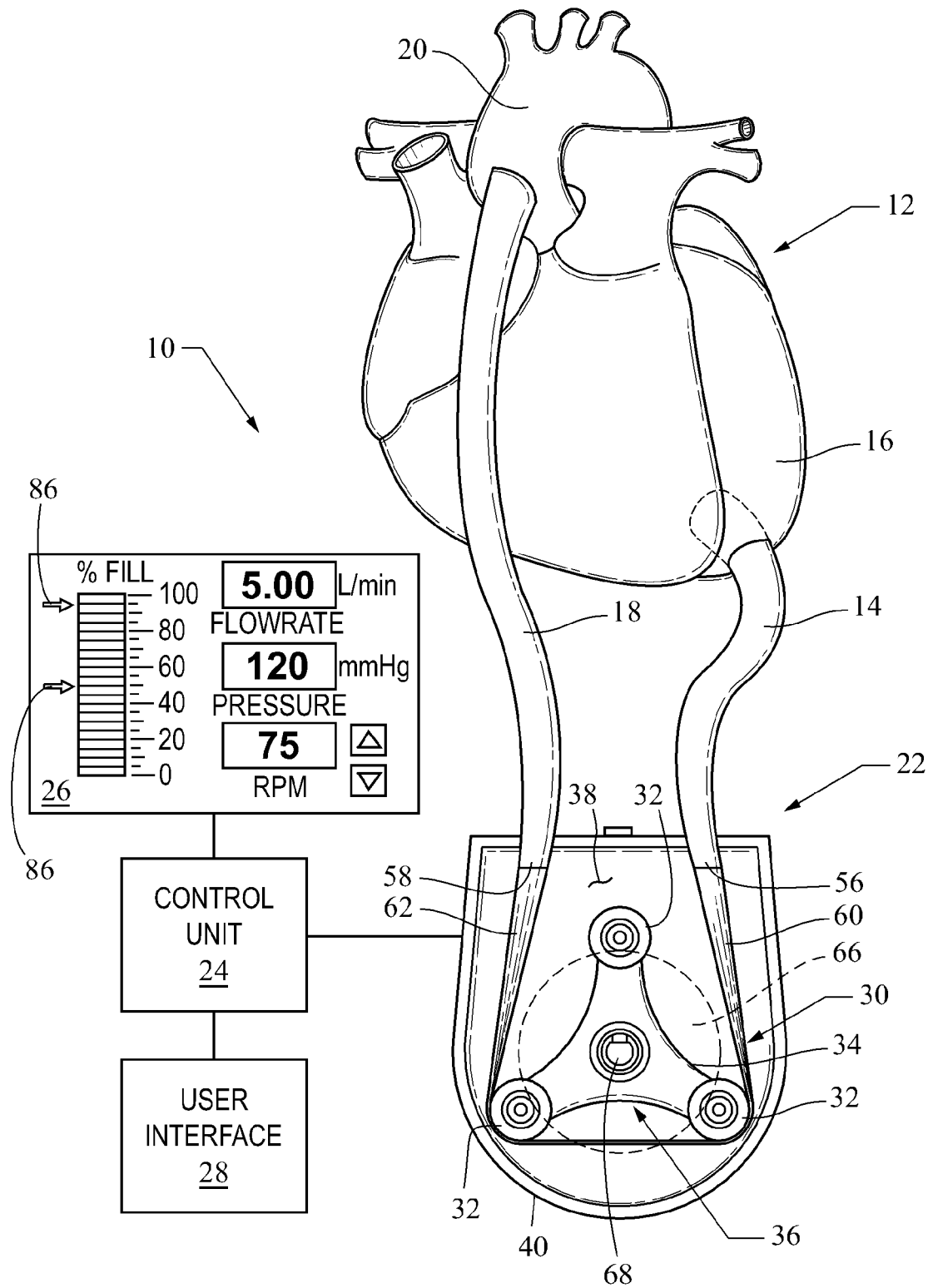
FIG. 1 is a diagrammatic illustration of a system incorporating the principles of the present invention and being directly connected to a patient.

Referring now to the drawings, a system for providing a ventricular assist device to a patient is generally illustrated in FIG. 1 and designated at 10. As seen in FIG. 1, the system 10 is intended to be directly connected to the patient without the imposition of a venous reservoir or other such components between the system 10 and the patient. As illustrated in FIG. 1, the patient is generally depicted by the schematic representation of a heart, which is designated by reference numeral 12, but which may be other circulatory locations in the patient. The system 10, while depicted as being placed for left ventricular assist by being coupled to the heart via the placement of an intake catheter 14 in the left ventricle 16 and the placement of an outtake catheter 18 in the aorta 20 of the patient 12, it will be apparent that the system 10 may be used for right ventricular assist, bi-ventricular assist, pulmonary assist, isolated organ perfusion, isolated limb perfusion, hypothermia treatment, cancer treatment, whole body treatment, partial body treatment, dialysis, apheresis, and peritoneal dialysis (each with its own appropriate location of attachment of the system to the patient 12).

The system 10 generally comprises of a blood pump, hereinafter a ventricular assist device (VAD) 22, a control unit 24, a display 26, and a user interface 28, the latter of which may or may not be integral with the display 26.

The VAD 22 includes a collapsible conduit, which is herein referred to as the pump chamber 30. The pump chamber 30 is wrapped under tension around freely rotating rollers 32 that are themselves mounted on a rotor 34 to form a roller assembly 36. The rotor assembly 36 and the pump chamber 30 may be housed in an interior compartment 38 of an enclosure 40.

As seen in FIG. 2, the enclosure 40 preferably includes a movable top wall 42 connected to one or more side walls 44 and a bottom wall 46. When the top wall 42 is closed upon the side walls 44, the top wall 42 may optionally use polymeric gaskets or other materials to form an airtight seal of the interior compartment 38, thereby allowing a controlled vacuum to be applied. Applying such a vacuum to the interior compartment 38 allows for vacuum assisted drainage from the patient 12 to the system 10, which may be useful in overcoming pressure losses in the catheter from the patient 12 to the system 10.

Figure 5:
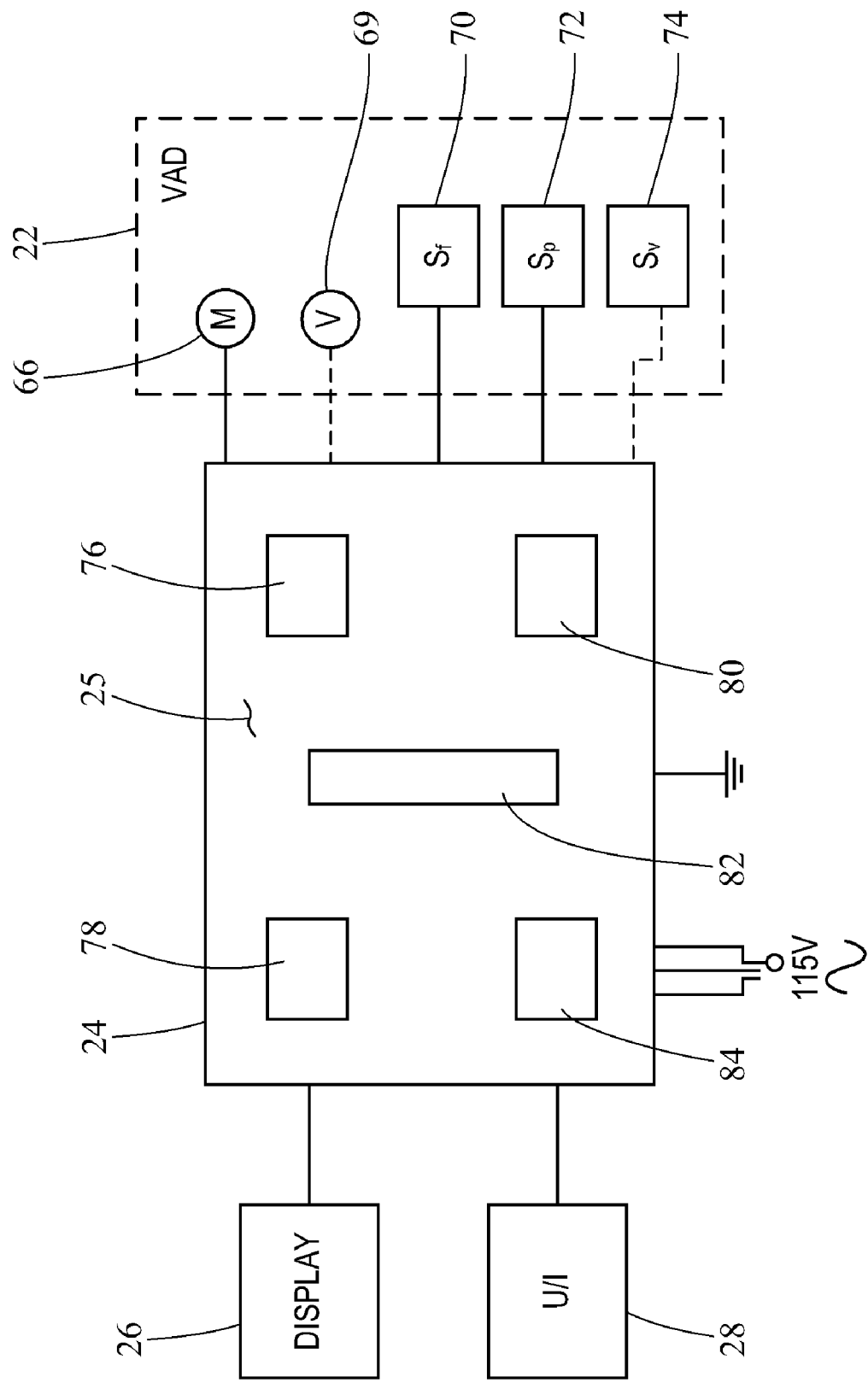
FIG. 5 is a schematic illustration of the of a system incorporating the principles of the present invention, apart from being connected to a patient.

For this purpose, a vacuum port 48 is provided in and through one of the walls 42, 44, 46 of the enclosure 40 and allows the interior compartment to be coupled to a vacuum pump (V) 69, (e.g., Schwarzer Precision SP270EC), which is schematically shown in FIG. 5. If vacuum assisted, the system 10 will preferably produce blood flows up to 5 L/min with inlet siphon pressures of 74 mmHg and maximum outlet pressures of 400 mmHg. This performance is suitable for emergency flow requirements of most adult patients. An inlet pressure of 74 mmHg is standard for ECMO support, which typically relies upon gravity drainage to the regulated roller pumps. Limiting the outlet pressure to 400 mmHg reduce hemolysis and eliminates the possibility of circuit rupture.

The enclosure 40 is preferably constructed of a biocompatible plastic material such as acrylic, and may be formed by injection molding the side walls 44 and the bottom wall 46 as a single, unitary piece, and the top wall 42 being a separate component mounted via a hinge 50 or other connection to the side walls 44. Alternatively, the various portions of the enclosure 40 can be individually formed and joined together by any appropriate means, such as ultrasonic welding or the use of adhesives.

The pump chamber 30 has a cross sectional shape that is collapsed and occluded in its "free" condition (i.e., when the pressure inside the pump chamber 30 equals the pressure acting on the exterior of the pump chamber 30), as seen in FIG. 3. The pump chamber 30 will prime only when fluid is supplied at a pressure above the pressure exterior to the pump chamber 30, such as the pressure in the interior compartment 38 of the enclosure 40. When fluid is being provided at such a positive pressure, the pump chamber 30 will begin to assume the lenticular cross sectional shape generally illustrated in FIG. 4.

To achieve the above occlusion in the free condition, the pump chamber 30 is constructed of from two sheets of a naturally flaccid flexible material 52, such as medical grade polyurethane sheets (e.g., Stevens MP-1880-P). The two sheets of material 52 are laid one atop the other and joined at their lateral edges 54 by a radio-frequency (RF) sealing machine (e.g., J.A. Callanan Co., Chicago, Ill., Model 60SB) welding thereby forming the pump chamber 30. In one preferred embodiment, the pump chamber 30 is formed with a constant width of 1.9 inches and a thickness of 0.023 inches for each sheet 52.

Additionally, as generally represented in FIG. 1, the pump chamber 30 may include an inlet tube 56 and an outlet tube 58, of an appropriately sized PVC tubing (preferably with an inner diameter of the inlet being ½ inch and an inner diameter of the outlet being ⅜ inch) RF welded to the longitudinal ends of the conduit defined by the two joined sheets 52. Fittings can be added to the tubes 56, 58 to locate and secure the tubes 56, 58 to enclosure of the VAD 22.

With the pump chamber 30 constructed in this manner, once an inlet region 60 of the pump chamber 30 is primed with fluid, as the rotor 34 rotates, fluid will be driven by peristaltic motion toward an outlet region 62 of the pump chamber 30. This pumping action is achieved without the use of a stator to occlude the pump chamber at the location of the rollers. Without a stator, the pressure generated by the VAD 22 is limited by the tension of the pump chamber 30 about the rollers 32. At a characteristic pressure limit (e.g., 300-400 mmHg), the fluid within the pump chamber 30 simply slips past the rollers and, resultingly, the pressure cannot further increase. Accordingly, one benefit of the present system is that the VAD 22 will not cause rupture of the blood circuit if the fluid outlet side of the system 10 is occluded, kinked or otherwise blocked.

The rotor 34 carries a plurality of freely supported rollers 34, which may be mounted on the ends of arms 64. By being freely supported, the rollers 32 are free to rotate relative to the rotor 34 and independent of the speed of rotation of the rotor 34. Preferably, the rollers 32 are equally spaced about the rotor assembly 36, are constructed of a polymeric bearing material and supported by polished, stainless steel pins affixed between the ends of the arms 64 of the rotor 34. As seen in the figures, the rotor assembly 36 includes three rollers 32. While illustrated with three rollers 32, it will be appreciated that at least two rollers 32 must be used and that a greater number of rollers 32 could be used. The rotor 34 may be formed of machined acrylic or a similar material formed into the desired configuration.

The rotor 34 is mounted to the output shaft of a motor 66, which is preferably a brushless DC gear motor (e.g., $\frac{1}{16}$ hp, 200 rpm max). The output shaft 68 extends through the bottom wall 46 of the enclosure 40, if an enclosure 40 is provided, and is provided with a sealed bearing of appropriate construction so as to maintain the sealed integrity of the interior compartment 38 when the compartment 38 is to be subjected to vacuum. DC torque motors are preferred in that they take advantage of the fact that the motor torque increases with the square of the diameter and directly with the motor's length. Thus, a relatively large diameter motor having a small length provides high torque and a compact geometry, which in turn allows for direct drive of the rotor assembly 36 without the use of gear assemblies, thereby avoiding expense, noise, weight and reliability concerns. Such motors 66 deliver smooth operation at low rotor speeds while in the presence of highly varying torque loads, the latter of which can be caused by the rollers pressurizing and discharging fluid from the pump chamber 30. This is an important issue during periods of unstable vascular volumes, which may be very highly variable during the first hours and days of vascular support. As previously noted, the system 10 is designed to be connected directly to the central vascular of the patient 12 without use of a fluid reservoir, although other components may be included in the system 10 depending on the particular application to for which the system 10 is being employed. When connected directly to the central vascular, variations in the preload and afterload of the vascular circuit act directly and immediately on the VAD 22, potentially affecting the balance of flow between the venous return to the VAD 22 and the output of the VAD 22.

Coupled to the VAD 22 is the control unit 24, which is typically provided with a number of individual controllers and drivers to effectuate operation of the various components of the system 10, including the motor 66, the display 26, the user interface 24, the vacuum pump 69 (if so provided) as well as various sensors, such as a flow sensor 70, a outlet pressure sensor 72 and a vacuum pressure sensor if provided (such as a piezoresistive vacuum pressure transducer (e.g., Keller Druck Series 2 PR). Such controllers and drivers have application specific functions and offer preconfigured software templates for easy implementation into the system 10. These components may include the devices listed in the table presented in FIG. 6. For example, the control 24 may include a motor controller 76 specifically developed for brushless DC motor control using shaft angle encoder based position feedback and sinusoidal commutation to achieve smooth, efficient rotation at low rpm. Alternatively, the components of the control unit 24 may have a single controller handling substantially all aspects of the system, various components of the control unit 24. The control unit 24 may include a printed circuit board 25 so as to provide a unified chassis for incorporation of the electronics into the system 10.

Preferably, the settling times for such a motor controller 76 should be less than or equal to 3 seconds for a change of plus or minus 10 rpm. Additionally, the rpm of the motor 66 should be able to be maintained at a target level of rpm with the VAD operating at maximum rpm and the outlet catheter 18 clamped shut. Finally, the motor 66 should be operable by the motor controller 76 in the expected range of about 10-75 rpm.

As suggested above, other components of the control unit 24 may include a display controller 78, a vacuum controller 80 (if so equipped), and a serial communication bus 82 for internal communications and coordination of the electronic functions. Additionally, the control unit 24 may further include a power input module 84, provided with an electromagnetic interference (EMI) filter an additional safety feature so as to meet the safety standards required for medical electrical equipment.

During operation of the system 10, the VAD 22 has an output flowrate that is independent of the after load, at least when operated within the physiologic pressures of the patient 12. Rather, the VAD 22 is preload dependent, meaning that the filling pressure determines the amount of stroke volume that is contained within the pump chamber 30 and delivered for each roller pass. As such, the filling pressure is a useful parameter for automatically balancing the pump flow with the venous return to the VAD 22.

If the patient's intravascular fluid volume increases, the rise in preload pressure will increase the stroke volume of the VAD 22 and with it, the flow output. In the event that the preload pressure is sufficient to fully fill the stroke volume, the pump output reaches a maximum value for a given rpm. As long as the venous return remains below this maximum stroke volume for a given rpm, the flows will be balanced and the VAD 22 will remain responsive to changes in intravascular volume. The graph presented in FIG. 7 illustrates the effect of various filling pressures on the output of the VAD 22 at various rpm speeds. As illustrated in FIG. 7, the filling pressures and it's relation to pump output (Q) is shown for three rotor speeds, namely 70 revolutions per minute, 100 revolutions per minute and 130 revolutions per minute.

In view of the above, the filling pressure or flow efficiency can be used in a clinical environment to allow the rpm to be set so as to achieve automatic flow balance. Additionally, the actual stroke volume may be used to monitor this balance, as the intravascular volume changes. For example, with a given rpm of the VAD 22, a maximum stroke volume can be defined based on bench measurements of the maximum flow under high filling pressures. Under clinical conditions, actual stroke volume can be derived from measured pump flows and the rpm, and expressed in terms of flow efficiency by the equation:

$$\text{FLOW EFFICIENCY} = (((Q \div \text{RPM}) \times (1 \div \text{ROLLERS})) \div SV_{max}) \times 100$$

wherein $SV_{max}$=the maximum stroke volume under high filling pressures; Q=output flowrate in liters per minute; RPM=the rotor speed in revolutions per minute; and ROLLERS=the number of rollers on the rotor.

When less than 100% filling occurs, by monitoring the output flow rate of the VAD 22 via the flow sensor 70, the flow efficiency can be calculated according to the above equation. This flow efficiency can then be outputted to the display 26 in a graphical presentation, as seen in FIG. 1. Less than 100% filling is an indication that the VAD 22 is operating below its full stroke volume and indicates that the VAD 22 can and will achieve flow balance, while remaining responsive to changes in the intravascular fluid status (volume) of the patient 12.

Figure 8:
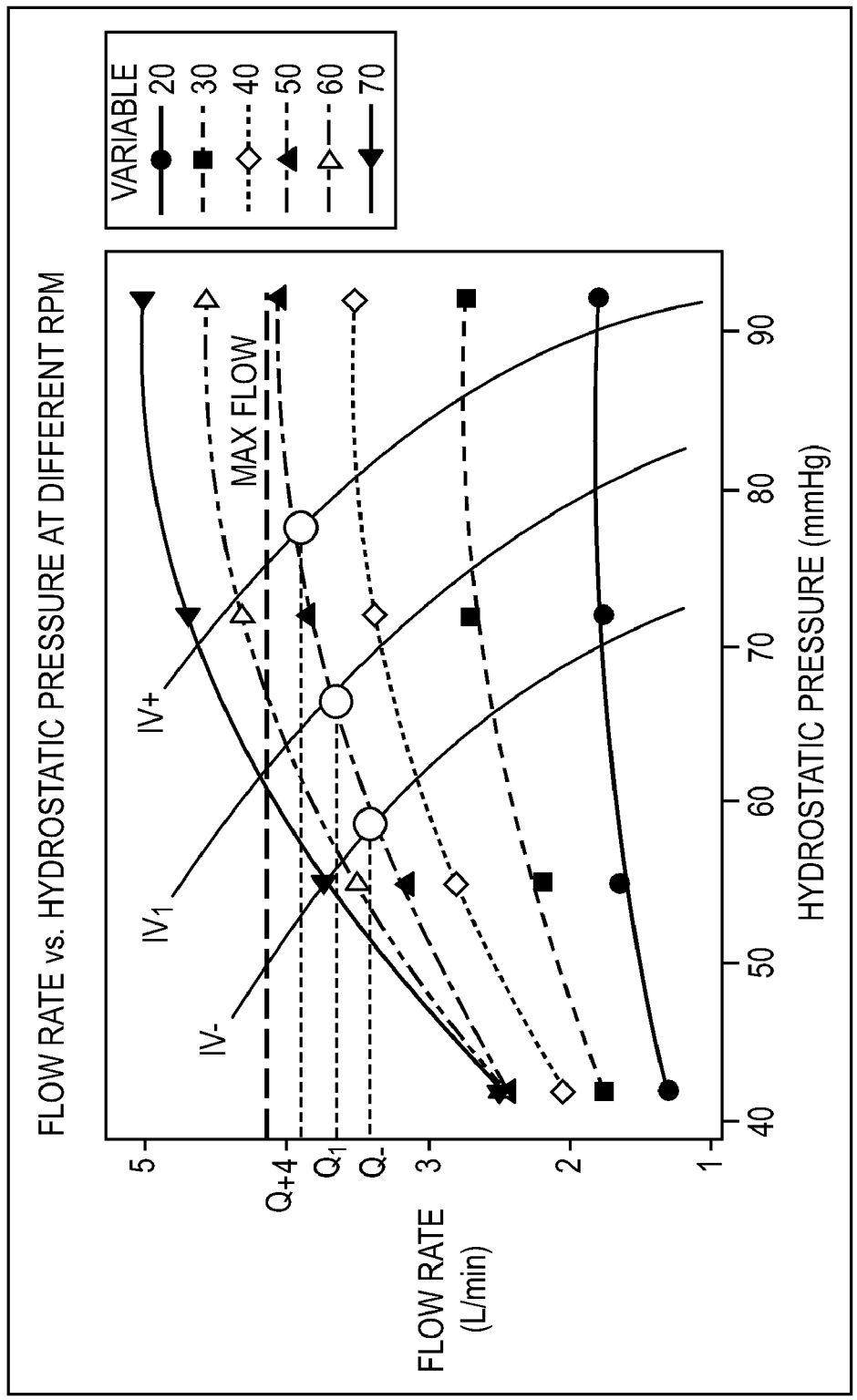
FIG. 8 is graphical representation of the relationship between inlet pressure and flow rate at various rotor speeds for an idealized patient and patients with increased and decreased fluid status relative to the idealized patient.

The concept of the preceding paragraph is graphically illustrated in FIG. 8, wherein the flow rate is presented for the preload pressure of a 4 inch diameter rotor and a 1.9 inch wide pump chamber at various rpm settings. $IV_1$ represents the idealized patient characteristic curve for initial vascular volume. $IV_+$ and $IV_-$ represent positive and negative changes to the intravascular volume. The intersection of the rpm curve indicates the operating point for flow rate and preload pressure. As intravascular volumes change, the intersection point with the rpm curve shifts, thereby providing automatic flow balance to the system. Thus, it can be seen that the flow efficiency indication is a powerful and innovative concept that offers a simple, easy to understand means of controlling and monitoring the operation of the VAD 22.

In the present system, the display 24 preferably illustrates the flow efficiency data such that the display accuracy is within plus or minus 5% of the calculated values. The user interface 28 may be configured to allow for the display resolution of the percent fill conditions to be adjusted, thereby accommodating finer or coarser increments of flow efficiency changes. Additionally, the user interface 28 and the control unit 24 will preferably allow for custom system configuration and the setting of user defined alarm limits 86. Such user defined alarm limits may be provided for flow efficiency, as shown in FIG. 1, as well as for the output flow rate and the outlet pressure of the VAD 22. In addition to the above performance criteria, the display 26 additionally presents the current speed of the VAD 22 in rpm. Finally, instead of providing the user interface 28 on a separate screen, the user interface 28 may be integrated into the display 26, such as utilizing a colored TFT LCD with touch screen capabilities.

The VAD 22 utilized in the system 10 of the present invention is a peristaltic pump that has safety features inherent in its design and that will respond to changes in the hemodynamic status of the patient with appropriate changes in output flow rate from the system. The above are accomplished without the need for manual adjustments to pump speed. Additionally, the system 10 has a low priming volume, prevents backflow, has no thrombogenic stagnation zones, is applicable to pediatric use, and has relatively low costs. Notably, the only disposable component of the present system is the blood contacting pump chamber 30.

The VAD 22 utilized in the present invention is a true "Starling" pump where flow rate is dependant upon RPM and filling pressure. The pump chamber 30, being naturally flat, only pumps whatever blood is delivered to it by venous drainage of the inlet catheter 14. If blood return is limited or stopped altogether, the pump chamber collapses and flow will decrease in proportion to the decreased filling. Even if the venous line is totally occluded (kinked), physically obstructed, or intermittently sucking into the vascular wall ("chattering"), negative pressure cannot be generated. As a result, cavitation and cavitation related hemolysis will not occur. Some of the safety features afforded include: 1) The pump cannot create suction pressure and requires a positive filling pressure for pumping to occur. This prevents tissue damage at the cannula site in the event of an interruption in venous flow from the patient. 2) Flow adjusts naturally to the volume status of the patient, obviating the need for specialized personnel to constantly change the pump speed. 3) The flat free condition nature of the pump chamber minimizes stress in the pump tubing, averting rupture while preventing backflow in the event of loss of power. 4) The maximum pressure generated by the pump is dictated by the tension of the pump chamber 30 around the rotor, and is set to ensure that the pump does not generate dangerously high outlet pressures. This feature prevents potential disruption of the blood circuit. 5) The peristaltic nature does not require use of flow valves, avoiding possible failures and stasis.

In an effort to address size and portability concerns, computational efforts were made to determine rotor diameter and pump chamber geometry (i.e. width, length, thickness) that would produce flow performance suitable for temporary adult application. With a pump rotor diameter of 4 inches and a pump chamber thickness of 0.023 inches and width of 1.9 inches, the VAD 22 can readily produce the flow required for temporary adult support, namely 5 L/min.

Vacuum assisted drainage will allow positioning of the pump in close proximity to the patient, reducing priming volume and blood transit time, and facilitating ambulation. A miniature printed circuit board may include pressure transducer amplification with adjustable pressure limit switches to activate the vacuum pump in the event pressure drops below a target set point and to stop the vacuum pump when the target level of vacuum is reached. A vacuum controller may include an adjustable hysteresis to prevent rapid cycling of the vacuum pump around the target pressure point.

Figure 9:
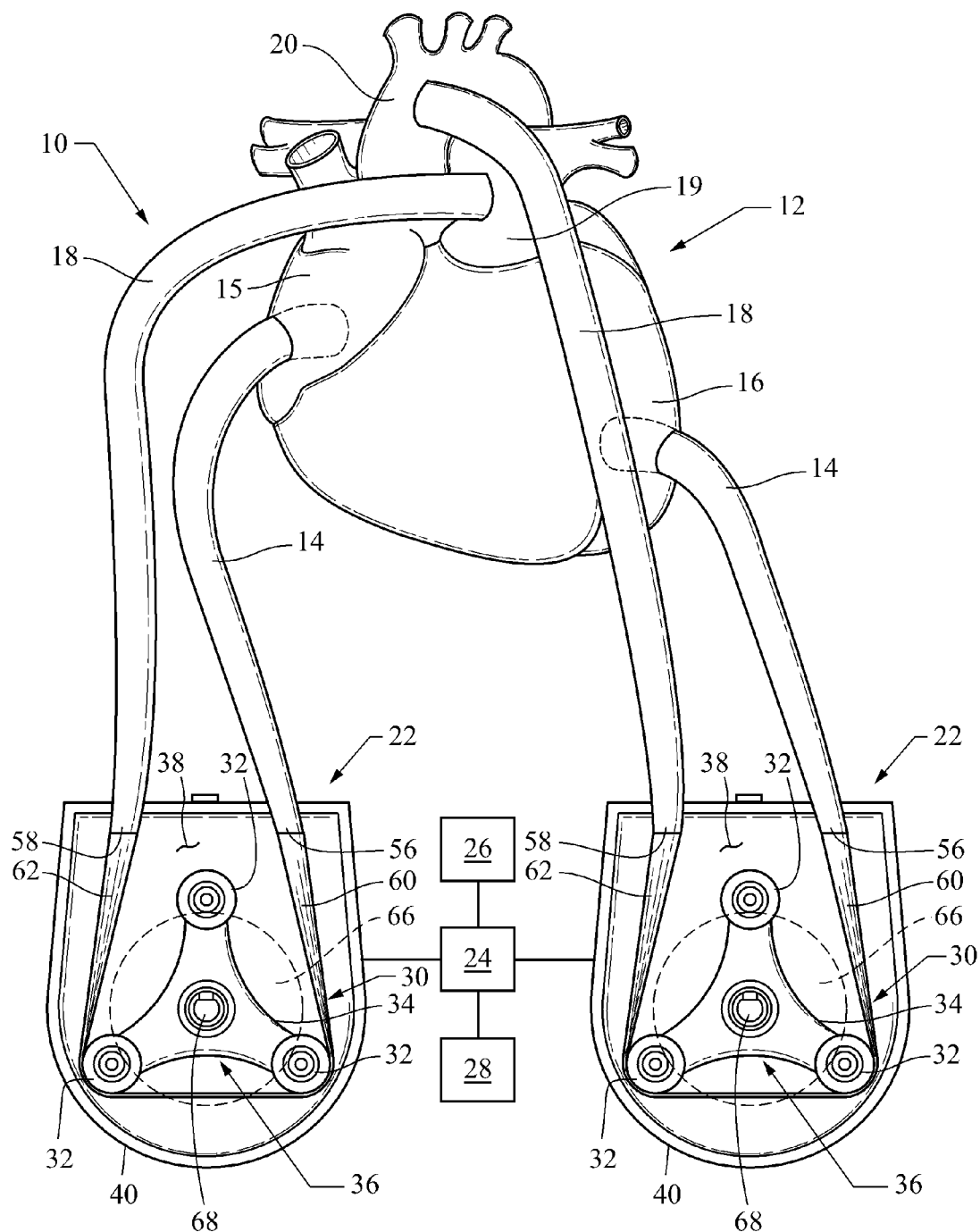
FIG. 9 is a diagrammatic illustration of a further embodiment of a system incorporating the principles of the present invention in a bi-ventricular assist application.

As a further embodiment of the present invention, FIG. 9 illustrates the implementation of the principles of the present invention in a bi-ventricular assist application. In this implementation, a second VAD 22 is connected by its intake catheter 14 to the heart 12 via the right atrium 15 and by its outtake catheter 18 to the pulmonary artery 19. The two VADs 22 utilize with a common controller 24, display 26 and user interface 28. In all other material respects, the two VADs 22 are of the same construction discussed above with reference to FIGS. 1-8.

As a person skilled in the art will readily appreciate, the above description is meant as an illustration of implementation of the principles this invention. This description is not intended to limit the scope or application of this invention in that the invention is susceptible to modification, variation and change, without departing from spirit of this invention, as defined in the following claims.

What is claimed is:

1. A system for controlling extracorporeal blood flow in a patient, the system comprising:
   a blood pump comprising a rotor, a plurality of rollers carried by the rotor, and a pump chamber extended in tension about the rollers;
   a sensor configured to measure an operating parameter of the blood pump;
   a controller coupled to the sensor, the controller calculating flow efficiency of the blood pump based on the operating parameter measured by the sensor and according to the equation $$\text{FLOW EFFICIENCY} = (((Q \div \text{RPM}) \times (1 + \text{ROLLERS})) \div SV_{max}) \times 100$$

wherein:
   $SV_{max}$=the maximum stroke volume under maximum filling pressure;
   Q=output flow rate in volume per minute;
   RPM=the rotor speed in revolutions per minute; and
   ROLLERS=the number of rollers on the rotor; and
   a display device coupled to the controller, the controller being configured to display on the display device the flow efficiency as determined by the controller.

2. The system of claim 1 wherein the controller is configured to graphically display the flow efficiency on the display device.

3. The system of claim 1 wherein the system comprises a user input coupled to the controller and configured to adjust at least one additional operating parameter of the blood pump.

4. The system of claim 1 wherein the blood pump comprises three rollers.

5. The system of claim 1 wherein the pump chamber is occluded in a free condition where the pressure acting on the interior of the pump chamber is equal to or less than the pressure acting on the exterior of the pump chamber.

6. The system of claim 1 wherein the pump chamber is defined by a pair of flexible side walls joined at lateral edges thereof and defining a passageway therebetween from a pump inlet to a pump outlet.

7. The system of claim 1 further comprising a pump enclosure defining an interior compartment, the interior compartment housing the rotor, rollers and pump chamber therein.

8. The system of claim 7 wherein the pump enclosure is substantially airtight and the interior compartment is coupled to a vacuum source.

9. The system of claim 1 further comprising a motor coupled to the rotor for rotation thereof, the controller being configured to control rotation of the rotor via the motor, the motor being a DC brushless motor.

10. The system of claim 1 wherein the controller is configured to display the rotational speed of the rotor on the display device.

* * * * *

UNITED STATES PATENT AND TRADEMARK OFFICE
CERTIFICATE OF CORRECTION

| | | |
|---|---|---|
| PATENT NO. | : 8,226,591 B2 | Page 1 of 1 |
| APPLICATION NO. | : 12/536349 | |
| DATED | : July 24, 2012 | |
| INVENTOR(S) | : Daniel E. Mazur | |

It is certified that error appears in the above-identified patent and that said Letters Patent is hereby corrected as shown below:

Col. 10, Line 1, Claim 1: "(1+Rollers)" should read --(1÷Rollers)--.

Signed and Sealed this
Fourth Day of September, 2012

David J. Kappos
*Director of the United States Patent and Trademark Office*